US008337880B2

(12) United States Patent
Chen et al.

(10) Patent No.: US 8,337,880 B2
(45) Date of Patent: Dec. 25, 2012

(54) OLIGO-SACCHARIDE ENHANCED OAT-BASED DRINK FOR TREATING HYPERLIPIDAEMIA AND HYPERGLYCEMIA AND IMPROVING GASTROINTESTINAL FUNCTION AND PROCESS FOR PREPARING THE SAME BY TRI-ENZYME HYDROLYSIS AND MICRO-PARTICLE MILLING

(75) Inventors: Kwan-Han Chen, Chiayi (TW);
Chun-Liang Chou, Chiayi (TW);
Chien-Yu Chen, Chiayi (TW);
Chien-Teng Fan, Chiayi (TW);
Hui-Min Lai, Chiayi (TW)

(73) Assignee: A.G.V. Products Corp., Chiayi (TW)

( * ) Notice: Subject to any disclaimer, the term of this patent is extended or adjusted under 35 U.S.C. 154(b) by 5 days.

(21) Appl. No.: 12/851,956

(22) Filed: Aug. 6, 2010

(65) Prior Publication Data
US 2012/0034341 A1 Feb. 9, 2012

(30) Foreign Application Priority Data
Aug. 10, 2009 (TW) .............................. 98126826 A

(51) Int. Cl.
*A61K 47/00* (2006.01)
*A23L 1/00* (2006.01)
*A23L 3/16* (2006.01)
*A47J 39/00* (2006.01)
*A23J 1/00* (2006.01)

(52) U.S. Cl. ........ 424/439; 426/520; 426/521; 426/618; 426/656

(58) Field of Classification Search ........................ None
See application file for complete search history.

(56) References Cited

U.S. PATENT DOCUMENTS

| 4,996,063 | A |  | 2/1991 | Inglett |
|---|---|---|---|---|
| 5,686,123 | A | * | 11/1997 | Lindahl et al. .................. 426/28 |
| 6,451,369 | B1 |  | 9/2002 | Triantafyllou |
| 6,685,974 | B2 |  | 2/2004 | Whalen |
| 2005/0031734 | A1 |  | 2/2005 | Duan et al. |

FOREIGN PATENT DOCUMENTS

| CN | 1566161 | 1/2005 |
|---|---|---|
| CN | 1966531 | 5/2007 |
| CN | 101341949 A | 8/2008 |

OTHER PUBLICATIONS

IUBMB "glucan 1,4-60 -glucosidase [EC 3.2.1.3]" IUBMB Enzyme Nomenclature, <http://www.chem.qmul.ac.uk/iubmb/enzyme/EC3/2/1/3.html>, created 1961, retrieved Dec. 7, 2011, 1 page.*
Machine Translation (pdf) for CN 101341949A; provided Aug. 29, 2012; published Jan. 14, 2009.*
Machine Translation (pdf; Google Translate) of Document published on the website of the Taiwan Dept of Health dated Jul. 7, 2009; provided Aug. 29, 2012. Website is: http://consumer.fda.gov.tw/Files/infohealthfood/%e6%a1%82%e6%a0%bc%e5%96%9d-%e7%9e%84%e7%87%95%e9%ba%a5-%e8%a1%9b%e7%bd%b2%e5%81%a5%e9%a3%9f%e5%a-d%97A00161_20090626.doc.*
Office Action dated Mar. 19, 2012 for 200910164086.0 which is a corresponding Chinese application that cites CN101341949A.
Office Action dated Jul. 17, 2012 for corresponding Taiwan application 098126826 that cites US 2005/0031734 and document published on the website of the Taiwan Department of Health (DOH).
Document published on the website of the Taiwan Department of Health (DOH) dated Jul. 7, 2009.
Abstract of the Taiwan Department of Health (DOH) dated Jul. 7, 2009 document published on the website.

* cited by examiner

*Primary Examiner* — Robert A Wax
*Assistant Examiner* — Jeffrey T Palenik
(74) *Attorney, Agent, or Firm* — WPAT, P.C.; Anthony King

(57) ABSTRACT

The invention relates to a tri-enzyme hydrolysis method for preparing an oligo-saccharide enhanced oat-based drink product useful in lowering cholesterol, triglyceride, blood sugar and improving gastrointestinal function which comprises not only oat β-glucan and but also a higher amount of isomalto-oligosacchride. In accordance with the invention, whole grains of oats are micronized to an average particle size of 100 microns prior to enzyme treatments, and a product of creamy milk-like texture is obtained without filtration so that nutrients of the whole grains of oats are retained. This invention enhances the value of oat-based processing to yield additional health-associated content and illness (such as hyperlipidaemia and hyperglycemia) prevention efficacy that are beyond the potential of oats per se.

9 Claims, 1 Drawing Sheet

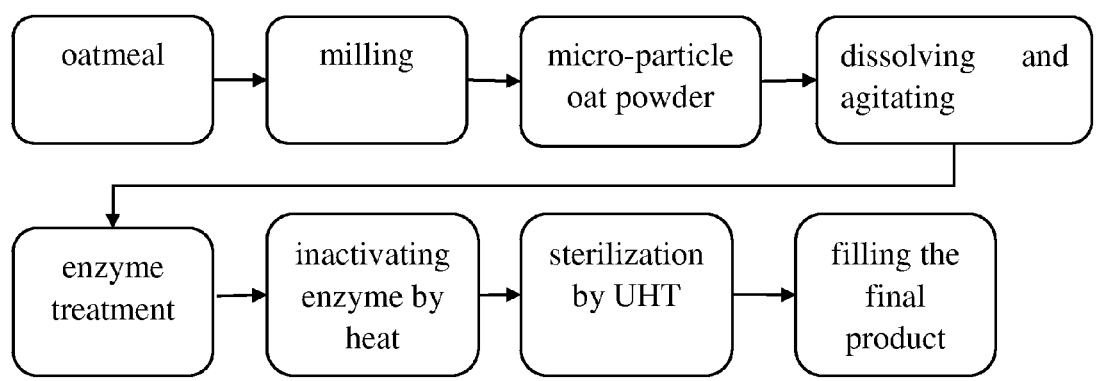

OLIGO-SACCHARIDE ENHANCED OAT-BASED DRINK FOR TREATING HYPERLIPIDAEMIA AND HYPERGLYCEMIA AND IMPROVING GASTROINTESTINAL FUNCTION AND PROCESS FOR PREPARING THE SAME BY TRI-ENZYME HYDROLYSIS AND MICRO-PARTICLE MILLING

FIELD OF THE INVENTION

The present invention relates to an oligo-saccharide enhanced oat-based drink useful in treating hyperlipidaemia and hyperglycemia and improving gastrointestinal function, and to a process for preparing the same by way of tri-enzyme hydrolysis.

BACKGROUND OF THE INVENTION

Oat has been considered a healthy cereal for a long time. It is rich in not only proteins, amino acids, essential fatty acids, vitamin B complex, and minerals such as iron, zinc and magnesium, but also water soluble and non-water soluble dietary fibers, especially β-glucan. Many medical or nutritional research papers have shown that oat β-glucan has the effect of preventing or alleviating cardiovascular diseases, diabetes, hypertension or constipation. Therefore, the nutrients in oat have been used as additives of various food products.

U.S. Pat. No. 4,996,063 discloses a method for producing a water-soluble dietary fiber composition by treating oat with α-amylase. The resultant powdered dietary fibers can be used as food additives and fat substitutes.

U.S. Pat. No. 5,686,123 discloses a homogenous and stable cereal suspension and the method of making the same, which comprises grinding rolled oats to a particle size of 0.8 to 1 mm, adding water having the temperature of 50 to 53° C. with agitation to form an oat slurry, treating the suspension with β-amylase to a viscosity of 3 to 0.1 Pas in the first enzyme treatment step, further treating the suspension with α-amylase to a viscosity of <0.5 Pas in the second enzyme treatment step, and subjecting the suspension to Ultra High Temperature (UHT) at the temperature of 137 to 138° C. for 3 to 4 seconds to obtain a homogenous and stable oat suspension.

U.S. Pat. No. 6,451,369 discloses a non-dairy, ready-to-use milk substitute and products made therewith. It discloses a method which comprises the steps of wet-milling oats to provide a pre-gelatinized suspension having a dry solids content of 10 to 15% w/w, and adding α-amylase and β-amylase simultaneously for hydrolysis of 1 to 2 hours to provide an oat suspension containing a significant amount of maltose and β-glucans.

U.S. Pat. No. 6,685,974 discloses a process for preparing an oat-based functional syrup, comprising the steps of blending an oat material having a granulation of less than #100 mesh (corresponding to 150 μm) with water to form a slurry, adding α-amylase to proceed an enzymatic treatment (68° C. for 2.5 hours), adding glucoamylase enzyme to proceed a further enzymatic treatment, and cooking the slurry to convert the slurry into an oat-based functional syrup. However, the product prepared with the process is substantially flavorless.

Furthermore, CN Patent Publication No. 1566161 discloses a process for preparing oat β-glucan, which comprises the steps of (1) preparing oat bran from oat, eradicating enzymes, (2) watering and stiffing at the temperature of 45-65° C., adjusting the pH value to 9-11, (3) separating and gathering filter liquor, charging alpha-amylase for processing, retaining 1-2 hours at 70-90° C., (4) cooling down to 10-30° C., adjusting the pH value to 4.5-5.0, agitating and stewing, settling proteins, (5) centrifuging to obtain the supernatant fluid, hyperconcentrating, charging alcohol isopropylicum into the concentration liquid, obtaining beta-gluglucosan gelatineous deposition, and (6) centrifuging the beta-gluglucosan gelatineous deposition, vacuum drying to obtain the beta-gluglucosan gelatineous end product.

In addition, CN Patent Publication No. 1966531 discloses a process for preparing oat β-glucan which comprises the steps of using oat bran as raw materials, crushing, microwave-assisted-extracting, adding amylase and glucoamylase, iso-electric-point-precipitating, centrifugating and separating, concentrating the supernatant, precipitating with ethanol, centrifugating and collecting the precipitation, solving with water, hydrolyzing with beta-glucanase, and spray-drying process to obtain the high-efficiency prebiotics oat β-glucan with enhanced intestinal and fecal bifidobacteria and actobacillus value-added effect.

Although the methods for preparing water soluble dietary fibers disclosed in the prior art can produce oat β-glucan with a high yield, their steps are complicated and involve enzymatic treatments which take a long time, resulting in high production costs. Furthermore, some products of the prior art have lost the natural flavor and aroma of oats and cannot provide the flavor of natural oats when consumed.

In addition to oat β-glucan, isomalto-oligosaccharide is known to lower the pH value of the intestine and enhance bowl movements. Isomalto-oligosaccharide can also inhibit the proliferation of harmful bacteria and decrease the toxic wastes generated in the metabolism of harmful bacteria, so it has the intestinal cleansing effect, and can vitalize bodily functions. However, the processes of the prior art do not provide an oat-based drink rich in both β-glucan and isomalto-oligosaccharide.

Accordingly, the present invention provides a process that combines micronized milling technique and enzymatic hydrolysis, wherein rolled oats are micronized and subjected to two-stage enzymatic treatments with α-amylase, and β-amylase and trans-glucosidase. In accordance with the invention, a homogenous, stable oat-based functional drink rich in β-glucan and isomalto-oligosaccharide can be produced.

SUMMARY OF THE INVENTION

In the first aspect, the present invention provides a via tri-enzymatic hydrolysis method for producing an oligo-saccharide enhanced oat-based drink useful in treating hyperlipidaemia and hyperglycemia and improving gastrointestinal function. The method comprises the following steps:
  (1) Providing a slurry of micronized oat powders having an average particle size of less than about 100 μm;
  (2) Treating the oat slurry with β-amylase to a viscosity of about 1 to 0.1 Pas, and with α-amylase and trans-glucosidase to a viscosity of 0.1 to 0.01 Pas;
  (3) Inactivating the enzymes with heating, and then cooling the reaction mixture; and
  (4) Subjecting the reaction mixture to Ultra High Temperature (UHT) to provide a stable oat-based drink with natural oat flavor and aroma.

A further aspect of the invention provides a micronized oat-based drink produced by the method of the invention, which comprises about 0.2 to 0.5% (w/w) β-glucan and about 1 to 3% (w/w) isomalto-oligosaccharide, and has micronized oat powders having an average particle size of less than about 50 μm.

BRIEF DESCRIPTION OF THE DRAWINGS

FIG. 1 is a flow chart showing an embodiment of the process of the present invention.

DETAILED DESCRIPTION OF THE INVENTION

In accordance with the process of the present invention, rolled oats are micronized to oat powders having an average particle size of less than about 100 µm, preferably less than about 75 µm. The micronized powders are then blended with water to form an oat slurry.

According to an embodiment of the present invention, rolled oats are micronized with a dry ball mill to oat powders having an average particle size of less than about 100 µm, preferably less than about 75 µm. The micronized powders are then blended with water, preferably having a temperature of about 30 to about 60° C., and more preferably about 50 to about 55° C., with agitation to form an oat slurry. Preferably, the weight ratio of the micronized oat powders to water is about 1:3 to about 1:15, corresponding to a dry solids content of about 6% w/w to about 25% w/w.

According to another embodiment of the present invention, rolled oats are directly micronized with a wet ball mill to oat powders having an average particle size of less than about 100 µm, preferably less than about 75 µm. Where necessary, water is added to obtain a slurry having a weight ratio of oat powders to water at about 1:3 to about 1:15, corresponding to a dry solids content of about 6% w/w to about 25% w/w. The wet micronized milling can be performed with hot water so that an oat slurry having the temperature of preferably about 30 to about 60° C., and more preferably about 50 to about 55° C., is obtained. Alternatively, the slurry can be heated to the desired temperature after milling. The temperature of the slurry enhances the dissolution of oat powders in water, which helps achieve the desired extent of extraction.

Suitably, the resultant oat slurry has a pH value of at least about 5, preferably about 5 to 8. In addition, as can be understood by persons having ordinary skill in the art, using de-ionized water will lead to an especially outstanding effect regardless of whether dry milling or wet milling is used. In a further aspect, for convenience, commercial pre-gelatinized rolled oats can be used to prepare the oat slurry.

The oat slurry is subjected to two-stage enzymatic treatments. The slurry is treated with β-amylase at the first stage to a viscosity of about 1 to 0.1 Pas, preferably less than about 0.3 Pas, and then with α-amylase and trans-glucosidase at the second stage to a viscosity of about 0.1 to 0.01 Pas, preferably less than about 0.05 Pas.

As can be appreciated by persons having ordinary skill in the art, the amount of enzymes and the reaction temperature and reaction time for the enzymatic treatments will vary along with many factors, such as the raw material employed, the enzyme added, and the desired viscosity of the end product. Persons having ordinary skill in the art can optimize the reaction conditions for the enzymatic treatments on the basis of the desired viscosity of the end product.

In an embodiment of the present invention, the amount of β-amylase added at the first enzyme treatment stage is about 0.1 to 1.0% (w/w), preferably about 0.2 to 0.5% (w/w), and the enzymatic reaction is performed at the temperature of about 40 to 70° C., preferably about 50 to 65° C.; the amounts of α-amylase and trans-glucosidase added at the second enzyme treatment stage are each about 0.1 to 1.0% (w/w), preferably about 0.2 to 0.5% (w/w), and the enzymatic reactions are operated at the temperature of about 40 to 70° C., preferably about 50 to 65° C. The total reaction time for the two enzymatic treatments is about 0.5 to 3 hours, preferably about 1 to 1.5 hours.

After the enzymatic treatments, the enzymes are inactivated with heating, and then the reaction mixture is cooled. According to an embodiment of the present invention, the inactivation is operated at the temperature of about 85 to 95° C., preferably about 90° C., for 3 to 5 minutes, preferably about 3 minutes, and then cooled to the temperature of about 50 to 70° C.

After the inactivation and cooling, the reaction mixture is then subjected to Ultra High Temperature (UHT) at about 130 to 140° C. for about 10 to 16 seconds to produce a micronized oat-based drink. Optionally, the drink product can be packed in an aseptic cool filling system. Furthermore, according to another embodiment of the present invention, the resultant micronized oat-based drink can be further subjected to dehydration and drying (such as spray-drying) to form stable oat-based drink powders convenient for transportation. The powders can be reconstituted with water before drinking.

The present invention has the following advantages:
(1) Providing an instant drink of whole grain cereals which conveniently avoids reconstitution procedures for making drinks from hulled cereals;
(2) Using α-amylase and β-amylase and trans-glucosidase at separate stages, allowing for optimized reactions which take only about 1 to 1.5 hours, thereby significantly shortening the processing time and saving costs; and
(3) Giving, through aseptic cool filling, the resultant product a prolonged shelf life at room temperature of up to 9 months.

In addition to the above advantages, the micronized oat-based drink produced by the method of the invention contains oat particles of a size of less than about 50 µm, preferably less than 30 µm, so it can be directly packed without the step of filtration; as a result, the nutrients of the whole grains of oats can be retained. In another aspect, the enzymatic treatments in accordance with the present invention produce not only β-glucan but also isomalto-oligosaccharide, which is 3 times higher in content than cereals.

The micronized oat-based drink produced according to the method of the present invention rich in β-glucan and isomalto-oligosaccharide comprises 0.2 to 0.5% w/w of β-glucan, preferably about 0.35 to 0.45% w/w, and about 1 to 3% w/w of isomalto-oligosaccharide, preferably about 1.5 to 2.5% w/w. It has been clinically confirmed that the micronized oat-based drink produced in accordance with the present invention can lower total cholesterol, low density lipoprotein cholesterol, and triglycerides in blood, and also is effective in reducing the fasting blood glucose level and improving metabolic syndromes. Thus, the micronized oat-based drink of the present invention has the potential for preventing and treating diseases such as hyperlipidaemia and hyperglycemia, and for improving gastrointestinal function.

Furthermore, the microzized oat-based drink of the present invention not only retains the natural flavor and aroma of oats but also has a milk-like taste, so the microzined oat-based drink of the present invention can be used as a milk substitute, especially suitable for patients with lactose intolerance. The microzined oat-based drink of the present invention can also be used as the base material for ice cream, oatmeal, yogurt, milk shake, health-care beverage or snacks, or be used to prepare seasoned cereal drinks containing components such as red beans and honey.

The following examples are provided to further describe the present invention and by no means limit the invention. Any modifications and variations which can be accomplished by persons having ordinary skill in the art are encompassed in the subject invention as disclosed in the specification and the accompanying claims.

EXAMPLES

1. Preparation of Oat Drink

An oat-based drink was produced as follows.
(a) Rolled oats were micronized with a dry ball mill to powders having an average particle size of about 75 μm.
(b) The micronized oat powders were blended with water (10 to 20% w/w; pH 5 to 8) and heated with agitation for 10 to 15 minutes at the temperature of 50 to 60° C. to form an oat slurry.
(c) The oat slurry was treated with enzymes as follows: 0.2 to 0.5% (w/w) β-amylase was added to proceed an enzymatic reaction (at the temperature of 50 to 65° C.). When the reaction mixture reached a viscosity of less than about 0.3 Pas, α-amylase and trans-glucosidase were added to proceed a further enzymatic reaction (at the temperature of 50 to 65° C.) so that the reaction mixture reached a viscosity of less than about 0.05 Pas. The enzymatic treatments took about 1 to 1.5 hours.
(d) The reaction mixture was heated for 3 minutes at the temperature of 90° C., and then cooled to 50 to 70° C.
(e) The reaction mixture was then subjected to Ultra High Temperature (UHT) at a temperature of 140° C. for 30 seconds and to aseptic cool filling. An oat-based drink rich in β-glucan (about 0.4% w/w) and isomalto-oligosaccharide (about 2.0% w/w) was obtained.
(f) The oat-based drink had an average particle size of less than about 30 μm.

2. Evaluation of Physiological Function

A clinical trial was conducted in accordance with the Assessments for Healthy Food Products: Blood Lipid Modulation announced by the Department of Health, Republic of China (Taiwan). Volunteers were screened on the basis of their blood biochemical values. Twenty-three subjects having a blood lipid level higher than the standard value (total cholesterol level higher than 200 mg/dL, triglyceride level higher than 200 mg/dL or low density lipoprotein cholesterol higher than 130 mg/dL) were recruited. Each subject had 680 mL of the oat-based drink of the present invention everyday for six weeks. During the trial, the subjects were not allowed to take any blood lipid lowering drugs or food supplements. Vein blood of the subjects were drawn prior to the trial (week 0), at the end of the third week of the trial (week 3) and at the end of the sixth weeks (week 6) and blood lipid and fasting blood glucose values were determined. The results were shown in Table 1.

(a) Effect on Serum Total Cholesterol (TC)

After consumption of the oat-based milk product of the present invention for three weeks, the serum TC concentration of the subjects significantly decreased from 215.8±36.6 mg/dL to 199.0±26.8 mg/dL (−7.8%; p<0.05); after six weeks, the serum TC concentration was 200.7±31.3 mg/dL, which was significantly lower than that of week 0 (p<0.05).

(b) Effect on Serum Triglyceride (TG)

After consumption of the oat-based milk product of the present invention for three weeks, the serum TG concentration of the subjects significantly decreased from 148.6±113.2 mg/dL to 110.0±70.4 mg/dL (−26%; p<0.05); after 6 weeks, the serum TG concentration was 115.5±75.1 mg/dL, which was significantly lower than that of week 0 (p<0.05).

(c) Effect on Serum Low Density Lipoprotein Cholesterol (LDL-C)

After consumption of the oat-based milk product of the present invention for three weeks, the serum LDL-C concentration of the subjects significantly decreased from 142.8±25.7 mg/dL to 128.0±24.1 mg/dL (−10.4%; p<0.05); after 6 weeks, the serum LDL-C concentration was 131.6±26.8 mg/dL, which was significantly lower than that of week 0 (p<0.05).

(d) Effect on Serum High Density Lipoprotein Cholesterol (HDL-C)

After consumption of the oat-based milk product of the present invention for three weeks, the serum HDL-C concentration of the subjects significantly decreased from 49.4±15.6 mg/dL to 46.4±14.4 mg/dL (p<0.05); after 6 weeks, the serum HDL-C concentration was 47.6±13.4 mg/dL, which slightly increased as compared with that of week 3, and was not statistically different from that of week 0 (p>0.05).

(e) Effect on Fasting Blood Glucose (Glucose)

After consumption of the oat-based milk product of the present invention for three weeks, the concentration of fasting blood glucose of the subjects significantly decreased from 110.2±20.8 mg/dL to 104.2±18.4 mg/dL (p<0.05); after 6 weeks, the fasting blood glucose concentration was 104.1±14.9 mg/dL, which was significantly lower than that of week 0 (p<0.05).

TABLE 1

Blood Lipid and Fasting Blood Glucose Levels[1]

| | Week[3] | Value |
|---|---|---|
| TC[2] (mg/dL) | 0 | 215.8 ± 36.6 |
| | 3 | 199.0 ± 26.8* |
| | 6 | 200.7 ± 31.3* |
| TG[2] (mg/dL) | 0 | 148.6 ± 113.2 |
| | 3 | 110.0 ± 70.4* |
| | 6 | 115.5 ± 75.1* |
| LDL-C[2] (mg/dL) | 0 | 142.8 ± 25.7 |
| | 3 | 128.0 ± 24.1* |
| | 6 | 131.6 ± 26.8* |
| HDL-C[2] (mg/dL) | 0 | 49.4 ± 15.6 |
| | 3 | 46.4 ± 14.4* |
| | 6 | 47.6 ± 13.4 |
| Glucose[2] (mg/dL) | 0 | 110.2 ± 20.8 |
| | 3 | 104.2 ± 18.4* |
| | 6 | 104.1 ± 14.9* |

[1]Data are expressed as means ± SD (n = 23).
[2]TC: Total Cholesterol; TG: Triglyceride; LDL-C: Low Density Lipoprotein Cholesterol; HDL-C: High Density Lipoprotein Cholesterol; Glucose: Fasting Blood Glucose
[3]Week 0: prior to trial; Week 3: end of the third week of trial; Week 6: end of the sixth week
*Statistically different as compared with that of week 0 (p < 0.05)

The micronized oat-based drink produced in accordance with the present invention has a good aromatic flavor, and a smooth and milk-like taste. It not only changes the traditional way of cereal flake consumption, but also significantly improves the nutritional values of oat products. According to the above results, the oat-based drink of the subject invention lowers not only the total cholesterol, low density lipoprotein cholesterol, and triglycerides in blood but also the fasting blood glucose level, and improves metabolic syndromes. The oat-based drink of the subject invention also has a high content of isomalto-oligosacchride, which has been proven in many clinical trials to be useful in maintaining digestive tract function, improving the intestinal flora ecology, promoting defecation, etc.

The above is merely an exemplary embodiment of the subject invention and should not be construed as the limitation of the present invention. Moreover, it will be understood that modifications and variations can be made by those of ordinary skill in the art without departing from the spirit and scope of the invention.

What is claimed is:

1. A method for producing an oligo-saccharide enhanced oat-based drink useful in treating hyperlipidaemia and hyperglycemia and improving gastrointestinal function, comprising the following steps:
   (1) Providing an oat slurry of micronized oat powders having an average particle size of less than about 100 μm;
   (2) Treating the oat slurry with β-amylase to a viscosity of about 0.3 to 0.1 Pas, and with α-amylase and trans-glucosidase to a viscosity of 0.05 to 0.01 Pas;
   (3) Inactivating the enzymes with heating, and then cooling the reaction mixture; and
   (4) Subjecting the reaction mixture to Ultra High Temperature (UHT) to provide a stable oligo-saccharide enhanced oat-based drink with natural oat flavor and aroma.

2. The method of claim 1, wherein the slurry used in step (1) is obtained by dry milling rolled oats to oat powders having an average particle size less than 75 μm, and blending the oat powders with water with agitation so that the weight ratio of the micronized oat powders to water in the oat slurry is about 1:3 to 1:15, corresponding to about a dry solids content of 6% w/w to 25% w/w.

3. The method of claim 1, wherein the slurry used in step (1) is obtained by wet milling rolled oats to oat powders having an average particle size of less than 75 μm, and optionally adding water such that the weight ratio of the micronized oat powders to water is about 1:3 to 1:15, corresponding to a dry solids content of about 6% w/w to 25% w/w.

4. The method of claim 1, wherein the oat slurry used in step (1) is prepared with de-ionized water and has the temperature of about 50 to about 60° C.

5. The method of claim 1, wherein the oat slurry used in step (1) has a pH value of at least about 5 to 8.

6. The method of claim 1, wherein the amounts of α-amylase, β-amylase and trans-glucosidase used in step (2) are each about 0.1 to 1.0% (w/w) and the enzymatic treatments are operated at the temperature of about 40 to about 70° C.

7. The method of claim 6, wherein the amounts of α-amylase, β-amylase and trans-glucosidase in step (2) are each about 0.2 to 0.5% (w/w) and the enzymatic treatments are operated at the temperature of about 50 to about 65° C.

8. The method of claim 1, further comprising the step of packing the micronized oat-based drink obtained in step (4) in an aseptic cool filling system.

9. The method of claim 1, further comprising the step of dehydrating the micronized oat-based drink obtained in step (4) to obtain micronized oat-based powders.

* * * * *